US010272044B2

(12) United States Patent
Zeigerson

(10) Patent No.: US 10,272,044 B2
(45) Date of Patent: *Apr. 30, 2019

(54) METHOD FOR THE PRODUCTION OF EMULSION-BASED MICROPARTICLES

(71) Applicant: Evonik Corporation, Parsippany, NJ (US)

(72) Inventor: Ehud Zeigerson, Ft. Collins, CO (US)

(73) Assignee: Evonik Corporation, Parsippany, NJ (US)

( * ) Notice: Subject to any disclaimer, the term of this patent is extended or adjusted under 35 U.S.C. 154(b) by 695 days.

This patent is subject to a terminal disclaimer.

(21) Appl. No.: 14/541,328

(22) Filed: Nov. 14, 2014

(65) Prior Publication Data

US 2015/0072928 A1 Mar. 12, 2015

Related U.S. Application Data

(62) Division of application No. 10/553,003, filed on Aug. 15, 2006, now Pat. No. 8,916,196.

(60) Provisional application No. 60/461,860, filed on Apr. 10, 2003.

(51) Int. Cl.
| | |
|---|---|
| *B01F 5/06* | (2006.01) |
| *A61K 9/16* | (2006.01) |
| *A61K 31/565* | (2006.01) |
| *B01F 3/08* | (2006.01) |
| *B01J 2/06* | (2006.01) |
| *C08J 3/14* | (2006.01) |
| *A61K 38/28* | (2006.01) |
| *A61K 38/38* | (2006.01) |
| *A61K 47/60* | (2017.01) |

(52) U.S. Cl.
CPC .......... *A61K 9/1694* (2013.01); *A61K 9/1617* (2013.01); *A61K 9/1635* (2013.01); *A61K 9/1641* (2013.01); *A61K 9/1647* (2013.01); *A61K 31/565* (2013.01); *A61K 38/28* (2013.01); *A61K 38/38* (2013.01); *A61K 47/60* (2017.08); *B01F 3/0807* (2013.01); *B01F 5/0696* (2013.01); *B01J 2/06* (2013.01); *C08J 3/14* (2013.01)

(58) Field of Classification Search
CPC ...... A61K 9/1694; A61K 38/38; A61K 38/28; A61K 9/1617; A61K 47/48215; A61K 9/1641; A61K 9/1635; A61K 31/565; A61K 9/1647; B01F 3/0807; B01F 5/0696; C08J 3/14; B01J 2/06

See application file for complete search history.

(56) References Cited

U.S. PATENT DOCUMENTS

| | | | |
|---|---|---|---|
| 3,664,963 A | 5/1972 | Pasin | |
| 3,780,195 A | 12/1973 | Balassa | |
| 3,790,905 A | 2/1974 | Sato | |
| 3,865,352 A | 2/1975 | Nelson et al. | 259/4 |
| 3,891,570 A | 6/1975 | Fukushima | |
| 4,165,219 A * | 8/1979 | Huber | G01N 30/34 210/656 |
| 4,171,981 A | 10/1979 | Austin et al. | |
| 4,183,681 A * | 1/1980 | Li | B01F 3/0811 366/336 |
| 4,299,501 A | 11/1981 | Patil | |
| 4,384,975 A | 5/1983 | Fong | |
| 4,389,330 A | 6/1983 | Tice | |
| 4,501,501 A * | 2/1985 | Edwards | B01F 3/12 118/600 |
| 4,897,268 A | 1/1990 | Tice | |
| 4,933,105 A | 6/1990 | Fong | |
| 5,112,604 A | 5/1992 | Beaurline et al. | 424/490 |
| 5,407,609 A | 4/1995 | Tice | |

(Continued)

FOREIGN PATENT DOCUMENTS

| | | |
|---|---|---|
| AU | 2004259209 | 2/2005 |
| CN | 102935069 | 2/2013 |

(Continued)

OTHER PUBLICATIONS

Hovekamp; "Experimental and Numerical Investigation of Porous Media Flow with regard to the Emulsion Process," 2002, A doctoral dissertation submitted to the Swiss Federal Institute of Technology ZQrich, pp. 1-101.*
Harnby et al. editors, "Mixing in the Process Industries," 1992, Butterworth & Heinemann; Second edition, Chapter 12, Author: Godfrey JC, "Static Mixers," pp. 225-249.*
Final Office Action dated May 10, 2013 by USPTO for U.S. Appl. No. 11/799,700, filed May 1, 2007 (Inventor—Zeigerson; pp. 1-21).
RJ Podolsky. "The Structure of Water and Electrolyte Solutions." Circulation, vol. 21, May 1960, pp. 816-827.
Non-Final Office Action issued by USPTO dated May 2, 2013 for for U.S. Appl. No. 10/564,494, filed Jul. 15, 2004 (Inventor—Cook; pp. 1-17).

(Continued)

*Primary Examiner* — David J Blanchard
*Assistant Examiner* — Ivan A Greene
(74) *Attorney, Agent, or Firm* — Linda S. Li; Jason S. Ngul; Bernard Lau

(57) ABSTRACT

The apparatus and methods of the present invention are of use for the production of emulsion-based microparticles containing a biological or chemical agent. In particular, the apparatus provides a vessel; packing material situated inside such vessel and may further provide material capable of insertion into both ends of said vessel for enclosure of the packing material. In a particular embodiment, the apparatus is a packed bed apparatus. The methods include production of emulsion based microparticles containing a biological or chemical agent. The usefulness of the present invention is that the apparatus and methods of the present invention provide for a low-shear, non-turbulent, production of emulsion-based microparticles that provides a narrow, reproducible, particle size distribution, capable of use with both large and small volumes that is capable of being conveniently scaled up while providing predictable emulsion properties.

29 Claims, 2 Drawing Sheets

(56) References Cited

U.S. PATENT DOCUMENTS

| | | | |
|---|---|---|---|
| 5,534,269 A | 7/1996 | Igari et al. | |
| 5,538,739 A | 7/1996 | Bodmer | 424/501 |
| 5,629,277 A | 5/1997 | Plishka | |
| 5,654,008 A | 8/1997 | Herbert et al. | 424/489 |
| 5,733,566 A * | 3/1998 | Lewis | A61K 31/7048 424/422 |
| 5,776,885 A | 7/1998 | Orsolini et al. | |
| 5,814,342 A | 9/1998 | Okada et al. | 424/493 |
| 5,846,562 A * | 12/1998 | Yanai | A61K 9/1617 424/439 |
| 5,869,103 A | 2/1999 | Yeh et al. | 424/501 |
| 5,876,761 A | 3/1999 | Bodmer et al. | |
| 6,120,805 A | 9/2000 | Spenlehauer et al. | 424/489 |
| 6,194,006 B1 | 2/2001 | Lyons et al. | 424/489 |
| 6,217,893 B1 | 4/2001 | Pellet et al. | 424/426 |
| 6,270,700 B1 | 8/2001 | Ignatious | |
| 6,281,254 B1 | 8/2001 | Nakajima | |
| 6,290,983 B1 | 9/2001 | Rickey | 424/426 |
| 6,379,704 B2 * | 4/2002 | Wright | A61K 9/1647 264/4.1 |
| 6,440,493 B1 | 8/2002 | Gibson et al. | 427/213.3 |
| 6,706,289 B2 | 3/2004 | Lewis | |
| 6,740,634 B1 | 5/2004 | Saikawa et al. | 514/2 |
| 6,953,593 B2 | 10/2005 | Juhrts | |
| 7,388,032 B2 | 6/2008 | Saikawa et al. | 514/772.1 |
| 8,916,196 B2 * | 12/2014 | Zeigerson | A61K 9/1635 424/489 |
| 2001/0035352 A1 | 11/2001 | Ozerov | |
| 2002/0028216 A1 * | 3/2002 | Donovan | A61K 9/0024 424/236.1 |
| 2002/0142050 A1 | 10/2002 | Straub | |
| 2002/0155158 A1 | 10/2002 | Lewis et al. | 424/486 |
| 2003/0134800 A1 | 7/2003 | Yamamoto et al. | |
| 2006/0228414 A1 | 1/2006 | Cook | |
| 2007/0092574 A1 | 4/2007 | Cook | |
| 2007/0207211 A1 | 9/2007 | Zeigerson | |

FOREIGN PATENT DOCUMENTS

| | | |
|---|---|---|
| EP | 1829529 | 9/2007 |
| EP | 2548550 | 1/2013 |
| JP | 10-109024 | 4/1998 |
| JP | 10-273447 A | 10/1998 |
| JP | 11-349688 | 12/1999 |
| JP | 01-108976 | 4/2001 |
| WO | WO-1991/015193 A1 | 10/1991 |
| WO | WO 1995/013799 | 5/1995 |
| WO | WO 97/04747 | 2/1997 |
| WO | WO 1997/041837 | 11/1997 |
| WO | WO 1998/032423 | 7/1998 |
| WO | WO-1998/043660 A1 | 10/1998 |
| WO | WO-1999/36099 A1 | 7/1999 |
| WO | WO-2000/062761 A1 | 10/2000 |
| WO | WO 2001/34120 | 5/2001 |
| WO | WO-2002/036169 A2 | 5/2002 |
| WO | WO-2002/041765 A2 | 5/2002 |
| WO | WO-2002/058672 A2 | 8/2002 |
| WO | WO-2002/061469 A2 | 8/2002 |
| WO | WO-2003/002092 A2 | 1/2003 |
| WO | WO-2003/092585 A2 | 11/2003 |
| WO | WO 2004/078147 | 9/2004 |
| WO | WO 2004/091494 | 10/2004 |
| WO | WO 2005/003180 | 1/2005 |
| WO | WO 2005/009356 | 2/2005 |
| WO | WO 2005/009356 A3 | 2/2005 |
| WO | WO 2005/009357 | 2/2005 |

OTHER PUBLICATIONS

CAS Registry Records for 25832-58-0, 532-02-5, 2169-87-1, 18396-51-5, 14206-62-3, 17273-79-9, 23520-54-9, All entered STN Nov. 16, 1984. 7 pages.

Final Office Action issued by USPTO dated Aug. 9, 2013 for for U.S. Appl. No. 10/564,494, filed Jul. 15, 2004 (Inventor—Cook; pp. 1-20) 1512328.

Carrasquillo, K.G. et al., Controlled Delivery of the Anti-VEGF Aptamer EYE001 with Poly(lactic-co-glycolic) Acid Microspheres, Invest. Opthalmol. Vis. Sci., Jan. 2003, Vo. 44, No. 1, pp. 290-299.

Kobayashi, I. et al., "Silicon Array of Elongated Through-Holes for Monodisperse Emulsion Droplets," AIChE Journal, Aug. 2002, vol. 48, No. 8, pp. 1639-1644.

Response to Office Action filed on Mar. 8, 2013 for CA Pat. App. No. 2,516,107, which is a national phase of Intl. Pat. App. No. PCT/US2004/011485, filed on Apr. 12, 2004 [Inventor—Zeigerson; Applicant—PR Pharmaceuticals] [7 pages].

Office Action dated Sep. 12, 2012 for CA Pat. App. No. 2,516,107, which is a national phase of Intl. Pat. App. No. PCT/US2004/011485, filed on Apr. 12, 2004 [Inventor—Zeigerson; Applicant—PR Pharmaceuticals] [2 pages].

Office Action dated Dec. 19, 2012 for CN Pat. App. No. 201110028030.X, which is divisional of CN Pat. App. No. 2004800008408.8, national phase of Intl. Pat. App. No. PCT/US2004/011485 filed Apr. 12, 2004 [Inventor—Zeigerson; Applicant—PR Pharmaceuticals] [8 pages].

Intention to Grant European Patent dated Oct. 26, 2012 for EP Pat. App. No. 04750117.6, which is a national phase of Intl. Pat. App. No. PCT/US2004/011485 filed on Apr. 12, 2004 [Inventor—Zeigerson; Applicant—Pharmaceuticals] [35 pages].

Extended European Search Report dated Jan. 4, 2013 for EP Pat. App. No. 12159499.8, which was filed on Mar. 14, 2012 [Inventor—Zeigerson; Applicant—Surmodics Pharmaceuticals, Inc.] [8 pages].

Final Office Action dated Mar. 4, 2013 for JP Pat. App. No. 2009-296315, which is a divisional of JP Pat. App. No. 2006-532408, national phase of Intl. Pat. App. No. PCT/US2004/011485, filed on Apr. 12, 2004 [Inventor—Zeigerson; Applicant—PR Pharmaceuticals] [2 pages].

Official Action dated Aug. 31, 2012 for JP Pat. App. No. 2009-296315, which is a divisional of JP Pat. App. No. 2006-532408, national phase of Intl. Pat. App. No. PCT/US2004/011485, filed on Apr. 12, 2004 [Inventor—Zeigerson; Applicant—PR Pharmaceuticals] [3 pages].

Response to Non-Final Office Action filed on Jan. 4, 2013 for U.S. Appl. No. 11/799,700, which was filed on May 1, 2007 [Inventor—Zeigerson; Applicant—PR Pharmaceuticals, Inc.] [5 pages].

Non-Final Office Action dated Oct. 4, 2012 for U.S. Appl. No. 11/799,700, which was filed on May 1, 2007 [Inventor—Zeigerson; Applicant—PR Pharmaceuticals, Inc.] [18 pages].

Office Action dated Nov. 23, 2012 for CA Pat. App. No. 2,533,592, which is a national phase of Intl. App. No. PCT/US2004/022817, filed on Jul. 15, 2004 [Inventor—Cook; Applicant—PR Pharmaceuticals] [4 pages].

Response to Office Action filed on Aug. 31, 2012 for CA Pat. App. No. 2,533,592, which is a national phase of Intl. App. No. PCT/US2004/022817, filed on Jul. 15, 2004 [Inventor—Cook; Applicant—PR Pharmaceuticals] [15 pages].

Office Action dated Mar. 1, 2012 for CA Pat. App. No. 2,533,592, which is a national phase of Intl. Pat. App. No. PCT/US2004/022817, filed on Jul. 15, 2004 [Inventor—Cook; Applicant—PR Pharmaceuticals] [3 pages].

Office Action dated Jan. 30, 2013 for EP Pat. App. No. 04778361.8, which is a national phase of Intl. Pat. App. No. PCT/US2004/022817, filed on Jul. 15, 2004 [Inventor—Cook; Applicant—PR Pharmaceuticals] [6 pages].

Reply to Communication from Examining Division filed on Nov. 8, 2011 for EP Pat. App. No. 04778361.8, which is a national phase of Intl. Pat. App. No. PCT/US2004/022817, filed on Jul. 15, 2004 [Inventor—Cook; Applicant—PR Pharmaceuticals] [7 pages].

Communication from the Examining Division dated Jan. 29, 2013 for EP Pat. App. No. 11187401.2, which is a divisional of EP 04778361.8, national phase of Intl. Pat. App. No. PCT/US2004/022817, filed on Jul. 15, 2004 [Inventor—Cook; Applicant—PR Pharmaceuticals] [6 pages].

Amendment filed on Oct. 25, 2012 for EP Pat. App. No. 11187401.2, which is a divisional of EP 04778361.8, national phase of Intl. Pat. App. No. PCT/US2004/022817, filed on Jul. 15, 2004 [Inventor—Cook; Applicant—PR Pharmaceuticals] [6 pages].

(56) References Cited

OTHER PUBLICATIONS

Extended European Search Report dated Mar. 28, 2012 for EP Pat. App. No. 11187401.2, which is a divisional of EP 04778361.8, national phase of Intl. Pat. App. No. PCT/US2004/022817, filed on Jul. 15, 2004 [Inventor—Cook; Applicant—PR Pharmaceuticals] [9 pages].
Office Action dated Dec. 16, 2011 for JP Pat App. No. 2006-521134, which is a national phase of Intl. Pat. App. No. PCT/US2004/022817, filed on Jul. 15, 2004 [Inventor—Cook; Applicant—PR Pharmaceuticals] [3 pages].
Applicant Initiated Interview Summary dated Oct. 11, 2012 for U.S. Appl. No. 10/565,401, which was filed on Jan. 20, 2006 [Inventor—Cook; Applicant—PR Pharmaceuticals, Inc.] [3 pages].
Response to Final Office Action filed on Oct. 4, 2012 for U.S. Appl. No. 10/565,401, which was filed on Jan. 20, 2006 [Inventor—Cook; Applicant—PR Pharmaceuticals, Inc.] [11 pages].
Applicant Initiated Interview Summary dated Sep. 24, 2012 for U.S. Appl. No. 10/565,401, which was filed on Jan. 20, 2006 [Inventor—Cook; Applicant—PR Pharmaceuticals, Inc.] [3 pages].
Final Office Action dated Jun. 4, 2012 for U.S. Appl. No. 10/565,401, which was filed on Jan. 20, 2006 [Inventor—Cook; Applicant—PR Pharmaceuticals, Inc.] [10 pages].
Response to Non-Final Office Action filed on Apr. 9, 2012 for U.S. Appl. No. 10/565,401, which was filed on Jan. 20, 2006 [Inventor—Cook; Applicant—PR Pharmaceuticals, Inc.] [11 pages].
Applicant Initiated Interview Summary dated Mar. 22, 2012 for U.S. Appl. No. 10/565,401, which was filed on Jan. 20, 2006 [Inventor—Cook; Applicant—PR Pharmaceuticals, Inc.] [3 pages].
Response to Office Action filed on Oct. 10, 2012 for CA Pat. App. No. 2,532,302, which is a national phase of Intl. Pat. App. No. PCT/US2004/022816, filed on Jul. 15, 2004 [Inventor—Cook; Applicant—PR Pharmaceuticals] [11 pages].
Office Action dated Apr. 10, 2012 for CA Pat. App. No. 2,532,302, which is a national phase of Intl. Pat. App. No. PCT/US2004/022816, filed on Jul. 15, 2004 [Inventor—Cook; Applicant—PR Pharmaceuticals] [2 pages].
Decision of Rejection dated Aug. 3, 2012 for CN Pat. App. No. 200480026606.7, which is a national phase on Intl. Pat. App. No. PCT/US2004/022816, filed on Jul. 15, 2004 [Inventor—Cook; Applicant—PR Pharmaceuticals] [6 pages].
Office Action dated Jan. 30, 2013 for EP Pat. App. No. 04778360.0, which is a national phase of Intl. Pat. App. No. PCT/US2004/002816, filed on Jul. 15, 2004 [Inventor—Cook; Applicant—PR Pharmaceuticals] [6 pages].
Reply to Communication filed on Nov. 8, 2011 for EP Pat. App. No. 04778360.0, which is a national phase of Intl. Pat. App. No. PCT/US2004/022816, filed on Jul. 15, 2004 [Inventor—Cook; Applicant—PR Pharmaceuticals] [14 pages].
Extended European Search Report and Opinion dated May 14, 2012 for EP Pat. App. No. 11187402.0, which is a divisional of EP 04778360.0, national phase of Intl. Pat. App. No. PCT/US2004/022816, filed on Jul. 15, 2004 [Inventor—Cook; Applicant—PR Pharmaceuticals] [9 pages].
Office Action dated Dec. 16, 2011 for JP Pat. App. No. 2006-520347, which is a national phase of Intl. Pat. App. No. PCT/US2004/022816, filed on Jul. 15, 2004 (Inventor—Cook; Applicant—PR Pharmaceuticals] [3 pages].
Reply to Communication from Examining Division filed on Nov. 29, 2011 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-15).
Office Action dated Dec. 16, 2011 for JP Pat App. No. 2006-521134, which is national phase of Intl. App. No. PCT/US2004/022817, filed on Jul. 15, 2004 (Inventor—Cook; Applicant—PR Pharmaceuticals; pp. 1-5).
Response to Office Action filed on Oct. 26, 2011 for CA Pat. App. No. 2,533,302, which is national phase of Intl. App. No. PCT/US2004/022816, filed on Jul. 15, 2004 (Inventor—Cook; Applicant—PR Pharmaceuticals; pp. 1-15).

Office Action dated Dec. 23, 2011 for CN Pat. App. No. 200480025606.7, which is national phase of Intl. App. No. PCT/US2004/022816, filed on Jul. 15, 2004 (Inventor—Cook; Applicant—PR Pharmaceuticals; pp. 1-11).
Buwalda, R. "Molecular Aggregation in Water the Interplay of Hydrophobic and Electrostatic Interactions." University of Groningen, Doctoral Dissertation, Nov. 19, 2001. Table of Contents only. 10 pages.
Buwalda, R. "Molecular Aggregation in Water the Interplay of Hydrophobic and Electrostatic Interactions," "Chapter 5 Wormlike Micellar and Vesicular Phases in Aqueous Solutions of Single-Talled Surfactants with Aromatic Counter Ions." Nov. 19, 2001, pp. 97-118.
Johnson, P.L., "Materials Safety Data Sheet. Sorbitol 70% Solution," Paddock Laboratories Inc. Minneapolis, MN, Dec. 10, 1991, pp. 1-4.
Materials Safety Data Sheet, Sodium Cholate, Sciencelab.com, Nov. 6, 2008, pp. 1-6.
Notice of Acceptance issued by Australian IP Office dated Mar. 22, 2010 for AU Pat. App. No. 2004253853, which is national phase of Intl. Pat. App. No. PCT/US2004/011485 filed Apr. 12, 2004 (Inventor—Ziegerson; Applicant—PR Pharmaceuticals; pp. 1-3).
Examiner's Report issued by Australian IP Office dated Feb. 24, 2010 for AU Pat. App. No. 2004253853, which is national phase of Intl. Pat. App. No. PCT/US 2004/011485 filed Apr. 12, 2004 (Inventor—Ziegerson; Applicant—PR Pharmaceuticals; pp. 1-2).
Response to Office Action filed by Applicant dated Jan. 18, 2010 for AU Pat. App. No. 2004253853, which is a national phase of Intl. Pat. App. No. PCT/US2004/011485 filed Apr. 12, 2004 (Inventor—Ziegerson; Applicant—PR Pharmaceuticals; pp. 1-15).
Examiner's Report issued by Australian IP Office dated Sep. 9, 2009 for AU Pat. App. No. 2004253853, which is national phase of Intl. Pat. App. No. PCT/US2004/011485 filed Apr. 12, 2004 (Inventor—Ziegerson; Applicant—PR Pharmaceuticals; pp. 1-2).
Response to Office Action filed by Applicant dated Aug. 15, 2011 for CA Pat. App. No. 2,516,107, which is national phase of Intl. Pat. App. No. PCT/US2004/011485 filed Apr. 12, 2004 (Inventor—Ziegerson; Applicant—PR Pharmaceuticals; pp. 1-17).
Office Action issued by Canadian IP Office dated Feb. 16, 2011 for CA Pat. App. No. 2,516,107, which is national phase of Intl. Pat. App. No. PCT/US2004/011485 filed Apr. 12, 2004 (Inventor—Ziegerson; Applicant—PR Pharmaceuticals; pp. 1-2).
Certificate of Patent dated Apr. 6, 2011 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-17).
Response to Office Action filed on Sep. 3, 2010 for CN Pat. App. No. 2004800008408.6, which is national phase of Intl. Pat. App. No. PCT/US2004/011485 filed Apr. 12, 2004 (Inventor—Ziegerson; Applicant—PR Pharmaceuticals; pp. 1-5).
Office Action dated Jun. 18, 2010 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-5).
Response to Office Action filed on Apr. 22, 2010 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-8).
Office Action dated Feb. 12, 2010 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-5).
Response to Office Action filed on Jan. 15, 2010 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-6).
Office Actton dated Oct. 23, 2009 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-6).
Preliminary Amendment filed on Aug. 17, 2009 for CN Pat. App. No. 2004800008408.8, which is national phase of Intl. Pat. App. No.

(56) References Cited

OTHER PUBLICATIONS

PCT/US2004/011485 filed Apr. 12, 2004 (Inventor—Ziegerson; Applicant—PR Pharmaceuticals; pp. 1-14).
Communication from Examining Division dated Jul. 19, 2011 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-7).
Reply to Communication from Examining Division filed on Sep. 14, 2010 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-9).
Communication from Examining Division dated Mar. 4, 2010 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-14).
Supplemental Search Report dated Oct. 28, 2009 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-3).
Preliminary Amendment filed on Dec. 30, 2005 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-6).
Indian Letters Patent Document issued on Apr. 29, 2010 for IN Pat. App. No. 4743/DELNP/2005, which is national phase of Intl. Pat. App. No. PCT/US2004/011485 filed Apr. 12, 2004 (Inventor—Ziegerson; Applicant—PR Pharmaceuticals; pp. 1).
Response to Examination Report filed on Dec. 30, 2009 for IN Pat. App. No. 4743/DELNP/2005, which is national phase of Intl. Pat. App. No. PCT/US2004/011485 filed Apr. 12, 2004 (Inventor—Ziegerson; Applicant—PR Pharmaceuticals; pp. 1-7).
Examination Report dated Jan. 14, 2009 for IN Pat. App. No. 4743/DELNP/2005, which is national phase of Intl. Pat. App. No. PCT/US2004/011485 filed Apr. 12, 2004 (Inventor—Ziegerson; Applicant—PR Pharmaceuticals; pp. 1-2).
Final Office Action dated Apr. 2, 2010 for JP Pat. App. No. 2006-532408, which is national phase of Intl. Pat. App. No. PCT/US2004/011485 filed Apr. 12, 2004 (Inventor—Ziegerson; Applicant—PR Pharmaceuticals; pp. 1-2).
Response to Office Action filed on Dec. 25, 2009 for JP Pat. App. No. 2006-532408, which is national phase of Intl. Pat. App. No. PCT/US2004/011485 filed Apr. 12, 2004 (Inventor—Ziegerson; Applicant—PR Pharmaceuticals; pp. 1-12).
Office Action dated Aug. 31, 2009 for JP Pat. App. No. 2006-532408, which is national phase of Intl. Pat. App. No. PCT/US2004/011485 filed Apr. 12, 2004 (Inventor—Ziegerson; Applicant—PR Pharmaceuticals; pp. 1-3).
Preliminary Amendment filed on Jul. 26, 2010 for JP Pat. App. No. 2009-296315, which is which is divisional of JP Pat. App. No. 2006-532408, filed Apr. 12, 2004 (Inventor—Ziegerson; Applicant—PR Pharmaceuticals; pp. 1-8).
Response to Final Office Action/Request for Continued Examination filed by Applicant on May 5, 2010 for U.S. Appl. No. 11/799,700, filed May 1, 2007 (Inventor—Zeigerson; pp. 1-8).
Final Office Action dated Jan. 5, 2010 by USPTO for U.S. Appl. No. 11/799,700, filed May 1, 2007 (Inventor—Zeigerson; pp. 1-11).
Response to Non-Final Office Action filed on Aug. 27, 2009 for U.S. Appl. No. 11/799,700, filed May 1, 2007 (Inventor—Zeigerson; pp. 1-9).
Non-Final Office Action dated Apr. 29, 2009 by USPTO for U.S. Appl. No. 11/799,700, filed May 1, 2007 (Inventor—Zeigerson; pp. 1-12).
Response to Restriction Requirement filed on Feb. 9, 2009 for U.S. Appl. No. 11/799,700, filed May 1, 2007 (Inventor—Zeigerson; pp. 1-10).
Restriction Requirement issued by USPTO dated Jan. 12, 2009 for U.S. Appl. No. 11/799,700, filed May 1, 2007 (Inventor—Zeigerson; pp. 1-7).

Response to Restriction Requirement filed on Oct. 21, 2008 for U.S. Appl. No. 11/799,700, filed May 1, 2007 (Inventor—Zeigerson; pp. 1-10).
Restriction Requirement issued by USPTO dated Apr. 21, 2008 for U.S. Appl. No. 11/799,700, filed May 1, 2007 (Inventor—Zeigerson; pp. 1-11).
Non-Final Office Action issued by USPTO dated Oct. 7, 2011 for for U.S. Appl. No. 10/565,401, filed Jul. 15, 2004 (Inventor—Cook; pp. 1-8).
Response to Final Office Action/Request for Continued Examination filed on Dec. 2, 2010 for for U.S. Appl. No. 10/565,401, filed Jul. 15, 2004 (Inventor—Cook; pp. 1-5).
Final Office Action issued by USPTO dated Aug. 3, 2010 for for U.S. Appl. No. 10/565,401, filed Jul. 15, 2004 (Inventor—Cook; pp. 1-6).
Response to Non-Final Office Action filed on May 24, 2010 for for U.S. Appl. No. 10/565,401, filed Jul. 15, 2004 (Inventor—Cook; pp. 1-8).
Non-Final Office Action issued by USPTO dated Feb. 23, 2010 for for U.S. Appl. No. 10/565,401, filed Jul. 15, 2004 (Inventor—Cook; pp. 1-7).
Response to Restriction Requirement filed on Oct. 15, 2009 for for U.S. Appl. No. 10/565,401, filed Jul. 15, 2004 (Inventor—Cook; pp. 1-3).
Restriction Requirement issued by USPTO dated Jun. 2, 2009 for for U.S. Appl. No. 10/565,401, filed Jul. 15, 2004 (Inventor—Cook; pp. 1-5).
Preliminary Amendment filed on Jan. 20, 2009 for for U.S. Appl. No. 10/565,401, filed Jul. 15, 2004 (Inventor—Cook; pp. 1-4).
Office Action issued by Canadian IP Office dated Feb. 8, 2011 for CA Pat. App. No. 2,533,592, which is national phase of Intl. App. No. PCT/US2004/022817, filed on Jul. 15, 2004 (Inventor—Cook; Applicant—PR Pharmaceuticals; pp. 1-3).
Decision of Granting Patent Right dated Oct. 16, 2009 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-2).
Request for Reexamination filed on Jun. 15, 2009 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-11).
Office Action dated Feb. 27, 2009 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-4).
Response to Office Action filed on Mar. 24, 2008 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-4).
First Office Action dated Oct. 19, 2007 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-6).
Communication from Examining Division dated Jan. 11, 2011 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-6).
Reply to Communication from Examining Division filed on Apr. 29, 2010 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-7).
Communication from Examining Division dated Oct. 22, 2009 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-6).
Supplemental European Search Report dated Jun. 10, 2009 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-3).
Preliminary Amendment filed on Apr. 24, 2006 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-11).

(56) References Cited

OTHER PUBLICATIONS

Request for Hearing filed on Apr. 15, 2009 for IN Pat. App. No. 957/DELNP/2006, which is national phase of Intl. App. No. PCT/US2004/022817, filed on Jul. 15, 2004 (Inventor—Cook; Applicant—PR Pharmaceuticals; pp. 1).
Response to Examination Report filed on Mar. 25, 2009 for IN Pat. App. No. 957/DELNP/2006, which is national phase of Intl. App. No. PCT/US2004/022817, filed on Jul. 15, 2004 (Inventor—Cook; Applicant—PR Pharmaceuticals; pp. 1-16).
Examination Report dated Apr. 15, 2008 for IN Pat. App. No. 957/DELNP/2006, which is national phase of Intl. App. No. PCT/US2004/022817, filed on Jul. 15, 2004 (Inventor—Cook; Applicant—PR Pharmaceuticals; pp. 1-2).
Response to Office Action filed on Apr. 28, 2011 for JP Pat App. No. 2006-521134, which is national phase of Intl. App. No. PCT/US2004/022817, filed on Jul. 15, 2004 (Inventor—Cook; Applicant—PR Pharmaceuticals; pp. 1-5).
Office Action dated Nov. 1, 2010 for JP Pat App. No. 2006-521134, which is national phase of Intl. App. No. PCT/US2004/022817, filed on Jul. 15, 2004 (Inventor—Cook; Applicant—PR Pharmaceuticals; pp. 1-9).
Response to Final Office Action/Request for Continued Examination filed on Nov. 22, 2010 for for U.S. Appl. No. 10/564,494, filed Jul. 15, 2004 (Inventor—Cook; pp. 1-12).
Final Office Action issued by USPTO dated May 26, 2010 for U.S. Appl. No. 10/564,494, filed Jul. 15, 2004 (Inventor—Cook; pp. 1-10).
Response to Non-Final Office Action filed on Mar. 17, 2010 for for U.S. Appl. No. 10/564,494, filed Jul. 15, 2004 (Inventor—Cook; pp. 1-12).
Non-Final Office Action issued by USPTO dated Nov. 19, 2009 for for U.S. Appl. No. 10/564,494, filed Jul. 15, 2004 (Inventor—Cook; pp. 1-13).
Response to Non-Final Office Action filed on Oct. 13, 2009 for for U.S. Appl. No. 10/564,494, filed Jul. 15, 2004 (Inventor—Cook; pp. 1-14).
Non-Final Office Action issued by USPTO dated Apr. 16, 2009 for for U.S. Appl. No. 10/564,494, filed Jul. 15, 2004 (Inventor—Cook; pp. 1-15).
Response to Restriction Requirement filed on Feb. 9, 2009 for for U.S. Appl. No. 10/564,494, filed Jul. 15, 2004 (Inventor—Cook; pp. 1-13).
Restriction Requirement issued by USPTO dated Dec. 8, 2009 for for U.S. Appl. No. 10/564,494, filed Jul. 15, 2004 (Inventor—Cook; pp. 1-11).
Examination Response filed on Apr. 13, 2011 for AU Pat. App. No. 2004259208, which is national phase of Intl. App. No. PCT/US2004/022816, filed on Jul. 15, 2004 (Inventor—Cook; Applicant—PR Pharmaceuticals; pp. 1-3).
Examiner's Report issued by Australian IP Office dated Apr. 8, 2011 for AU Pat. App. No. 2004259208, which is national phase of Intl. App. No. PCT/US2004/022816, filed on Jul. 15, 2004 (Inventor—Cook; Applicant—PR Pharmaceuticals; pp. 1).
Examiner's Report issued by Australian IP Office dated Aug. 3, 2009 for AU Pat. App. No. 2004259208, which is national phase of Intl. App. No. PCT/US2004/022816, filed on Jul. 15, 2004 (Inventor—Cook; Applicant—PR Pharmaceuticals; pp. 1-2).
Office Action issued by Canadian IP Office dated Apr. 27, 2011 for CA Pat. App. No. 2,533,302, which is national phase of Intl. App. No. PCT/US2004/022816, filed on Jul. 15, 2004 (Inventor—Cook; Applicant—PR Pharmaceuticals; pp. 1-3).
Response to Office Action filed on Jan. 21, 2010 for CN Pat. App. No. 200480026606.7, which is national phase of Intl. App. No. PCT/US2004/022816, filed on Jul. 15, 2004 (Inventor—Cook; Applicant—PR Pharmaceuticals; pp. 1-10).
Office Action dated Jul. 17, 2009 for CN Pat. App. No. 200480026606.7, which is national phase of Intl. App. No. PCT/US2004/022816, filed on Jul. 15, 2004 (Inventor—Cook; Applicant—PR Pharmaceuticals; pp. 1-15).

Communication from Examining Division dated Jan. 11, 2011 for EP Pat App. No. 04776360.0, which is national phase of Intl. App. No. PCT/US2004/022816, filed on Jul. 15, 2004 (Inventor—Cook; Applicant—PR Pharmaceuticals; pp. 1-6).
Reply to Communication filed on Apr. 29, 2010 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-9).
Communication from Examining Division dated Oct. 22, 2009 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-7).
Supplementary European Search Report dated Jun. 10, 2009 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-3).
Preliminary Amendment filed on Apr. 13, 2006 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-7).
Indian Letters Patent Document dated Jan. 29, 2009 for IN Pat. App. No. No. 706/DELNP/2006, which is national phase of Intl. App. No. PCT/US2004/022816, filed on Jul. 15, 2004 (Inventor—Cook; Applicant—PR Pharmaceuticals; pp. 1).
Supplemental Response to Examination Report filed on Jan. 9, 2009 for IN Pat. App. No. No. 706/DELNP/2006, which is national phase of Intl. App. No. PCT/US2004/022816, filed on Jul. 15, 2004 (Inventor—Cook; Applicant—PR Pharmaceuticals; pp. 1-2).
Response to Examination Report filed on Jan. 9, 2009 for IN Pat. App. No. No. 706/DELNP/2006, which is national phase of Intl. App. No. PCT/US2004/022816, filed on Jul. 15, 2004 (Inventor—Cook; Applicant—PR Pharmaceuticals; pp. 1-4).
Examination Report dated Jan. 11, 2008 for IN Pat. App. No. No. 706/DELNP/2006, which is national phase of Intl. App. No. PCT/US2004/022816, filed on Jul. 15, 2004 (Inventor—Cook; Applicant—PR Pharmaceuticals; pp. 1-2).
Response to Office Action filed on Apr. 27, 2011 for JP Pat App. No. 2006-520347, which is national phase of Intl. App. No. PCT/US2004/022816, filed on Jul. 15, 2004 (Inventor—Cook; Applicant—PR Pharmaceuticals; pp. 1-5).
Office Action dated Nov. 1, 2010 for JP Pat App. No. 2006-520347, which is national phase of Intl. App. No. PCT/US2004/022816, filed on Jul. 15, 2004 (Inventor—Cook; Applicant—PR Pharmaceuticals; pp. 1-7).
Office Action dated Aug. 3, 2010 in U.S. Appl. No. 10/565,401.
Office Action dated May 26, 2010 in U.S. Appl. No. 10/564,494.
Edlund and Albertson, "Degradable polymer microspheres for controlled drug delivery," In: Advances in Polymer Science, Abe et al. Ed., Springer-Verlag, Heidleberg, 2002, discloses many different methods for preparing microparticles (see pp. 98-101).
Franssen et al. "A Novel Preparation Method for Polymeric Microparticles Without the Use of Organic Solents," *Intl. J. Pharm.* 168:1-7, 1998.
Rothen-Weinhold et al., "Development and evaluation in vivo of a long-term delivery system for vapreotide, a somatostatin analog," *J. Contr. Rel.* 52:2005-213, 1998.
Rothen-Weinhold et al., "Stability studies of a somatostatin analogue in biodegradable implants," *Intl. J. Pharm.* 178:213-221, 1999.
Smith et al., "Evaluation of poly(lactic acid) as a biodegradable drug delivery system for parenteral administration," *Intl. J. Pharm.* 30:215-220, 1986.
Supplemental European Search Report dated Jun. 11, 2009, for International Application No. PCT/US2004/022816.
Supplemental European Search Report dated Jun. 10, 2009, for International Application No. PCT/US2004/022817.
International Preliminary Report on Patentability Chapter I, PCT/US2004/011485, dated Feb. 24, 2009.
International Search Report, PCT/US2004/011485, dated Mar. 21, 2008.
Written Opinion, PCT/US2004/011485, dated Mar. 21, 2008.
International Preliminary Report on Patentability Chapter I, PCT/US2004/022817, dated Feb. 2, 2006.

(56) References Cited

OTHER PUBLICATIONS

International Search Report, PCT/US2004/022817, dated Oct. 14, 2005.
Written Opinion, PCT/US2004/022817, dated Oct. 14, 2005.
International Search Report, PCT/US2004/022816, dated Jun. 9, 2005.
International Preliminary Report on Patentability Chapter 1, PCT/US2004/022816, dated Jan. 26, 2006.
Written Opinion, PCT/US2004/022816, dated Apr. 7, 2005.
Langer, "Drug delivery and targeting," *Nature* 392 (Supplement):5-10 (1998).

\* cited by examiner

Figure 1 – Packed Bed Apparatus
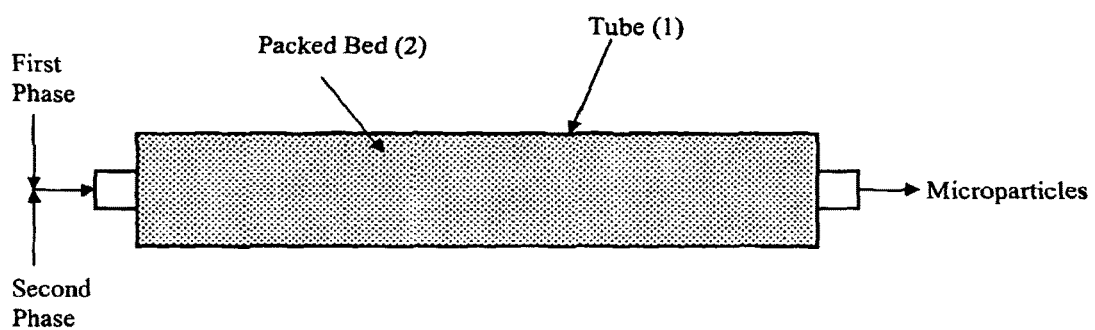

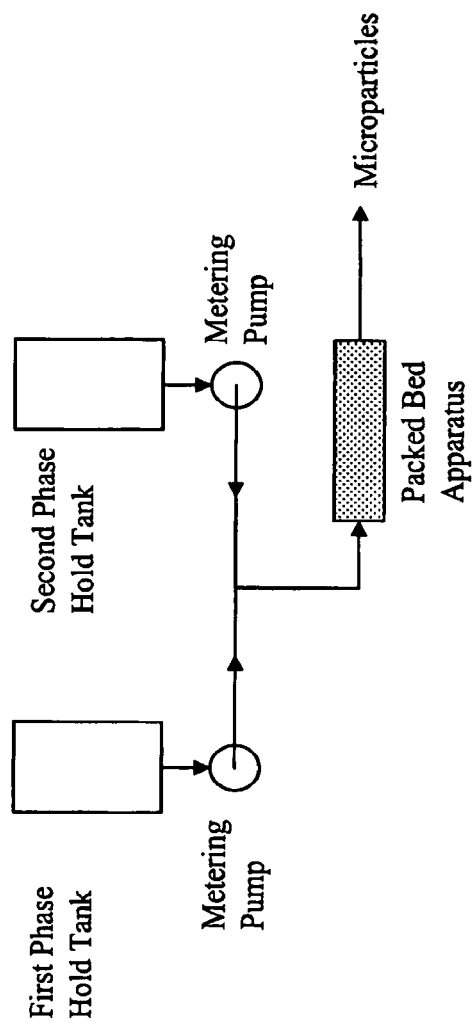
Figure 2 – A Typical Packed Bed Emulsification System

METHOD FOR THE PRODUCTION OF EMULSION-BASED MICROPARTICLES

CROSS REFERENCE TO RELATED APPLICATIONS

This application is a divisional of and claims priority to U.S. application Ser. No. 10/553,003, filed on Aug. 15, 2006, which claims priority from U.S. Provisional Patent Application No. 60/461,860 filed on Apr. 10, 2003.

FIELD OF THE INVENTION

The present apparatus and methods of using such apparatus relate to the field of manufacturing. More particularly, the disclosed apparatus and methods concern the production of emulsion-based microparticles and a method for producing emulsion-based microparticles containing biological or chemical agents.

BACKGROUND OF THE INVENTION

Several techniques for the production of microparticles containing biological or chemical agents by an emulsion-based manufacturing technique have been reported. In general, the methods have a first phase consisting of an organic solvent, a polymer and a biological or chemical agent dissolved or dispersed in the first solvent. The second phase comprises water and a stabilizer and, optionally, the first solvent. The first and the second phases are emulsified and, after an emulsion is formed, the first solvent is removed from the emulsion, producing hardened microparticles.

An alternative method involves the formation of a "double emulsion". In this method, a first phase, often called an "internal phase", is produced and normally consists of water, a biological or chemical agent, and, possibly, a stabilizer. A second-phase normally consists of an organic solvent and a polymer. The first and second phases are emulsified to form a water-in-oil "internal emulsion". A third-phase usually consists of water, a surfactant and, optionally, the second solvent. The internal emulsion is then emulsified again with the third phase to form an oil-in-water "external emulsion". After the external emulsion is formed, the organic solvent is removed from the emulsion, producing hardened microparticles.

Emulsions may be formed by a variety of techniques. One such technique is the use of a batch device for mixing the first and second phases under turbulent conditions such as with a stirrer as disclosed in U.S. Pat. No. 5,407,609. Other batch processes may employ a homogenizer or a sonicator. In another technique, an emulsion is formed by continuously mixing the first phase and second phase, in-line, using turbulent flow conditions, as in the use of an in-line dynamic mixer or an in-line static mixer such as described in U.S. Pat. No. 5,654,008.

When emulsions are created by a turbulent mixing device, such as static and dynamic mixers, a turbulent region exists where the two phases mix and the emulsion is formed. This mixing technique is problematic because turbulent mixers create areas of varying turbulence as some areas in the mixer produce a higher turbulence (typically closer to the blades and walls), while other areas produce lower turbulence (further away from blades and walls). Varying turbulence within the mixer results in a wide range of microparticle sizes, which can be undesirable.

Another problem with using turbulent mixing devices for producing microparticles is that a whole range of parameters such as flow rates, viscosities, densities, surface tension and temperature govern the level of turbulence inside the apparatus itself. The sensitivity of a turbulent process to the fluid flow and other physical properties makes it difficult to consistently produce a final product with the same properties. Batch to batch variation is not acceptable for the majority of microparticle products.

Another problem with turbulent mixing processes for the production of microparticles is that some active agents, such as proteins, are sensitive to high shear forces that are inherently part of turbulent mixing. Hence, these processes cannot be utilized to create microparticles with some common biological or chemical agents.

An additional difficulty with turbulent mixing processes relates to scalability. Turbulence, and the resulting microparticle properties, cannot be accurately predicted when changing the scale of production. This means that any time a change is made to the turbulent emulsion apparatus, a new set of experiments must be conducted in order to establish new guidelines for operation of the device in order to create the desired microparticle product. The need for repeated testing whenever scaling up production is expensive and time-consuming.

Turbulent-based emulsion devices also have physical limitations, specifically with their application of the laws of fluid dynamics. When using turbulent flow mixing devices, the dynamics of a particular mixer is correlated with a particular microparticle size and microparticle size distribution.

In order to achieve the same microparticle size and distribution when scaling up or scaling down, the same mixing turbulence must be produced in the larger or smaller mixer. As scaling up involves a change in the size of the mixer, a change in velocity (V) must be accomplished in order to compensate for the change in the diameter (D) of the mixer. Thus, application of a turbulent-based process for the formation of microparticles becomes especially difficult, and ultimately not practical, when very low flow rates are desirable because it is hard to achieve the desirable turbulence.

In the above-mentioned production processes, the resultant particle size is a function of the shear forces experienced by the two phases when mixed. Shear forces in these methods vary across the volume being mixed and, as a result, produce relatively broad particle size distributions. In the case of production processes dependent on turbulent flow, it is difficult to achieve turbulent flow conditions for low flow rates such as might be used during exploratory experiments with limited volumes, and the performance of larger devices is difficult to predict from results with small versions. Hence, there is little correlation between the results achieved on a small-scale in the laboratory and those achieved in later manufacture-sized production with turbulent flow based production processes.

An alternative method for producing an emulsion utilizes a packed bed emulsifier, as described in U.S. Pat. No. 4,183,681 ('681). The '681 patent describes the use of a packed bed emulsifier to form oil-in-water emulsions. Unfortunately, the emulsions disclosed do not form microparticles, are directed to applications with oil/water phase volume ratios equal to or greater than 1:1 and the packing materials that are found to be effective are not compatible with the need for clean and sterile apparatus such as required for microparticles containing therapeutic chemical or biological agents.

Other alternative emulsion forming techniques may employ filtration membranes or passage of fluids through a microchannel device as described in U.S. Pat. No. 6,281, 254. These methods require precision fabrication and can be cumbersome to scale up to production volumes.

Thus, a method is needed for forming emulsion-based microparticles that provides a narrow, reproducible, particle size distribution, capable of use with both large and small volumes, and is capable of being conveniently scaled up while providing predictable emulsion properties. Ideally, this method would utilize a non-turbulent emulsifier in order to allow its use with all chemical or biological agents.

SUMMARY OF THE INVENTION

In contrast to known methods of producing microparticles dependent on turbulent flow, such as that created with a static or dynamic mixer, the apparatus and methods of the present invention utilize laminar flow conditions to produce an emulsion that results in microparticles containing biological or chemical agents after solvent removal.

In a broad aspect of the present invention, a process for preparing an emulsion that produces microparticles containing biological or chemical agents after removal of solvent is provided.

In one embodiment, a first phase containing a solvent, an active agent and a polymer and a second phase containing a solvent is passed through a packed bed emulsifier under laminar flow conditions producing an emulsion that results in microparticles upon solvent removal.

In a second embodiment, a first phase containing a solvent and an active agent and a second phase containing a solvent and a polymer are combined to create an emulsion. In a particular embodiment, the emulsion is created in a packed bed apparatus, a mixer, a sonicator, a vortexer, a homogenizer, and the like. This emulsion is then passed through a packed bed apparatus under laminar flow conditions with a third phase containing a solvent in order to produce an emulsion that results in microparticles upon solvent removal.

In a third embodiment, a method of producing microparticles containing biological or chemical agents is provided via production of an emulsion under laminar flow conditions in a packed bed apparatus where such emulsion is capable of producing microparticles upon solvent removal. In a particular embodiment, the emulsion is produced from the mixture of a first and second phase. Such first and second phase may be immiscible with one another.

The first phase solvent may be any organic solvent or water. In a particular embodiment, the organic solvent is selected from the group consisting of methylene chloride, chloroform, ethylacetate, benzyl alcohol, diethyl carbonate and methyl ethyl ketone. The first phase may further comprise an emulsion stabilizer.

The second phase solvent may be any organic solvent or water. The second phase may further comprise an emulsion stabilizer.

Any emulsion stabilizer may be utilized with the present invention. In a particular embodiment, the stabilizer may be selected from the group consisting of poly(vinyl) alcohol), polysorbate, protein, poly(vinyl pyrrolidone), and the like.

The second phase may further comprise an additional solvent selected from the group consisting of an organic solvent or water.

The third phase solvent may be any organic solvent or water.

The active agent of the present invention may be any biological or chemical agent. In a particular embodiment, the active agent is selected from the group consisting of antioxidants, porosity enhancers, solvents, salts, cosmetics, food additives, textile-chemicals, agro-chemicals, plasticizers, stabilizers, pigments, opacifiers, adhesives, pesticides, fragrances, antifoulants, dyes, salts, oils, inks, cosmetics, catalysts, detergents, curing agents, flavors, foods, fuels, herbicides, metals, paints, photographic agents, biocides, pigments, plasticizers, propellants, solvents, stabilizers, polymer additives, an organic molecule, an inorganic molecule, antiinfectives, cytotoxics, antihypertensives, antifungal agents, antipsychotics, antibodies, proteins, peptides, antidiabetic agents, immune stimulants, immune suppressants, antibiotics, antivirals, anticonvulsants, antihistamines, cardiovascular agents, anticoagulants, hormones, antimalarials, analgesics, anesthetics, nucleic acids, steroids, aptamers, hormones, steroids, blood clotting factors, hemopoietic factors, cytokines, interleukins, colony stimulating factors, growth factors, growth factor analogs, fragments thereof, and the like.

The polymer of the present invention may be any polymer. In a particular embodiment, the polymer is selected from the group consisting of poly(d,l-lactic acid), poly(l-lactic acid), poly(glycolic acid), copolymers of the foregoing including poly(d,l-lactide-co-glycolide) (PLGA), poly(caprolactone), poly(orthoesters), poly(acetals), poly(hydroxybutryate) and the like.

In another broad aspect of the present invention, an apparatus capable of producing an emulsion that results in microparticles containing biological or chemical agents after solvent removal is provided. The apparatus includes a vessel and packing material.

Packing material of the present invention can be selected from the group consisting of metal, ceramic, plastic, glass and the like. In a particular embodiment, the packing material is glass or stainless steel. It may be in a shape selected from the group consisting of spheres, beads, pellets, chips, fibers, sponges, pillows and the like. In a particular embodiment, the beads are spherical. In an additional particular embodiment, the spherical beads range in diameter from 20 to 1000 microns.

BRIEF DESCRIPTION OF THE DRAWINGS

The following drawings form part of the present specification and are included to further demonstrate certain embodiments. These embodiments may be better understood by reference to one or more of these drawings in combination with the detailed description of specific embodiments presented herein.

FIG. 1. Illustrates an exemplary packed bed apparatus with various components according to an embodiment of the present invention.

FIG. 2. Illustrates an exemplary emulsion system for manufacturing microparticles containing a biological or chemical agent including a packed bed apparatus according to an embodiment of the present invention.

DETAILED DESCRIPTION OF THE INVENTION

The present invention provides an apparatus and methods of using such apparatus for the production of microparticles via an emulsion-based technique. In contrast to previously known methods for the production of emulsion-based microparticles, the present invention provides a non-turbulent, or laminar flow, process for producing microparticles with a narrow, reproducible, particle size distribution, capable of use with both large and small volumes with the capacity of being scaled up while providing-consistent predictable properties in the resulting larger batches. Microparticles containing many biological or chemical agents may be produced by the methods of the present invention.

The present invention overcomes disadvantages of previous methods of microparticle production through the use of a non-turbulent or laminar flow, packed bed system rather than a mixer. Both static and dynamic mixers create turbulent flow conditions associated with highly variable microparticle size distributions. The use of a packed bed system to create an emulsion provides for even droplets and resultant microparticle size distribution, as well as conditions suitable for many chemical or biological agents. Additionally, the apparatus and methods of the present invention can easily produce scalable results. Desirable batches of microparticles produced in the laboratory on a small scale can easily be reproduced on a larger manufacturing scale merely by utilizing the same packing material in a vessel with a larger diameter. This allows for the inexpensive and efficient scaling of the production process once the desired microparticles are produced on a small scale in the laboratory.

In a certain embodiment, the methods of the present invention provide a continuous process for making an emulsion for microparticle production in a wide range of flow rates and volumes. In some embodiments, the methods involve a process for making microparticles with a predetermined size distribution. In alternative embodiments, the methods provide a continuous process for making microparticles at very low flow rates.

Microparticles of the present invention may be made by any emulsion technique known in the art. In one embodiment, the method for producing an emulsion for microparticle production includes (1) preparing a first phase typically containing an organic solvent, a polymer, and one or more biologically active agents and/or chemicals; (2) preparing a second phase typically containing water as the second solvent, an emulsion stabilizer and optionally a solvent; (3) passing the first and second phases through a packed bed apparatus to form an "oil in water" type emulsion.

In another embodiment, the method for production of an emulsion includes (1) preparing a first phase typically containing an organic solvent and an emulsion stabilizer; (2) preparing a second phase typically containing water as the second solvent, one or more biologically active agents and/or chemicals, and a water soluble polymer; (3) passing the first and the second phases through a packed bed apparatus to form a "water in oil" type emulsion.

In a third embodiment, the invention provides methods for producing emulsions by (1) preparing a first phase containing an organic solvent and, optionally, an emulsion stabilizer; (2) preparing a second phase containing a second organic solvent, one or more biologically active agents and/or chemicals, and a polymer; (3) passing the first and the second phases through a packed bed apparatus to form an organic emulsion.

In yet another embodiment the invention provides methods for producing emulsions by (1) preparing a first phase typically containing water, one or more biologically active agents and/or chemicals and an emulsion stabilizer; (2) preparing a second phase typically containing an organic solvent and a polymer; (3) preparing a third phase typically containing water and optionally containing a stabilizer; (4) passing the first and the second phases through a packed bed apparatus to form a "water in oil" type emulsion; (5) passing the first emulsion and the third phase through a second packed bed apparatus to form an "oil in water" emulsion.

The apparatus and methods of using such apparatus to produce microparticles are not dependent on turbulent flow. The methods of making microparticles of the present invention work at laminar flow rates in contrast with prior methods of making microparticles. In the present invention, microparticles with a narrow and repeatedly precise particle size distribution can be produced. Additionally, they can be produced on a small scale and easily scaled-up to manufacturing size by merely altering the diameter of the vessel. This was not possible with prior turbulent flow methodologies. Surprisingly, making the emulsion within a laminar flow regimen solves many of the problems associated with turbulent emulsion-forming processes, as described above.

Packed Bed Apparatus

The apparatus of the present invention is a packed bed apparatus for the production of microparticles through an emulsion-based technique. Such apparatus may be a vessel of any shape capable of being filled with packing material that allows liquid to flow through it (See FIG. 1). The apparatus of the present invention may further provide a material capable of insertion into both ends for enclosure of materials in such apparatus. FIG. 1 illustrates an exemplary apparatus according to one embodiment of the present invention. In this embodiment, a tube (1) is filled with beads as packing material (2).

The apparatus of the present invention is packed with materials that force the liquids to flow through the gaps in between the packing material in order to get through the apparatus. The gaps in between the packing material inside the device may be viewed as many channels which cross each other's path repeatedly as the fluids flow through the bed.

In the present invention, the emulsion is made as the two fluids, or phases (typically oil and water), are flowing through the gaps inside the packing. As the two phases are flowing through the bed of solids, they cross each other's path repeatedly, and the continuous phase (usually the water) is dividing the discontinuous phase (usually the oil) into droplets, thus creating an emulsion. The discontinuous phase droplet size is being reduced repeatedly until a final droplet size is achieved. Once the discontinuous droplets have reached a certain size, they will not be reduced any further even if they continue flowing through the packing. This emulsion making mechanism allows the formation of a precisely sized emulsion at laminar flow conditions.

The very unique dynamics of a packed bed allow for the production of microparticles continuously at very low flow rates, not possible with mixing devices. This low flow rate enables the consistent production of high-quality microparticles in batches as small as 0.1 grams that maintain consistent particle size distribution. Additionally, these very unique flow dynamics also provide for scalability from laboratory to manufacturing sized batches.

The apparatus and methods of using such apparatus provide an emulsion-based process for making microparticles that is insensitive to flow rates within the laminar flow region. Unlike turbulent mixer-based process, the methods of the present invention are not sensitive to changes in the flow rates, when operated within a laminar flow region. The flow rate of use in the present invention can be any laminar flow rate. In a particular embodiment the flow rate is 0.0001 to 100 liter/minute.

The apparatus and methods of using such apparatus provide an emulsion-based process for making microparticles that is easily scalable from laboratory to manufacturing sized batches. A typical batch may demonstrate 10,000 fold scalability. In a particular batch, the size of the batch may be selected from the group consisting of, but not limited to, 0.1 gram, 1 gram, 10 grams, 50 grams, 100 grams, 250 grams, 0.5 kilograms, 1 kilogram, 2 kilogram, 5 kilograms, 10 kilograms, 15 kilograms, 20 kilograms, 25 kilograms, 30 kilograms, and the like. One method of increasing the scale of a batch of microparticles is to increase the diameter of the vessel. Such increase will function to increase the volume of emulsion through the vessel, thus directly increasing the size of the batch produced.

The apparatus and methods of using such apparatus provide an emulsion-based process for making microparticles that provides for tight control of the particle size distribution. Microparticle size distribution may be manipulated by altering the packing material size, shape and type; rearranging the inlet or outlet enclosures; alteration of the physical properties of the first, second or third phases; altering the length or width of the vessel and the like. For example, the final microparticle size can be determined by the size of the packing material, such as the diameter of a glass bead. Additionally, the length of the vessel may directly affect the particle size distribution.

The vessel of the present invention may be in any form capable of containing the packing material. In a particular embodiment, the apparatus is in the form of a tube. The cross section may be of any compatible shape including rectangular, square and round. In a particular embodiment, the cross section is approximately circular. The vessel may be of any length. In a particular embodiment, the length of the vessel may range from 1 cm to 100 meters. In another particular embodiment, such vessel is 10 to 50 cm.

Packing material of use in the present invention may be anything capable of inclusion within the device. In a particular embodiment, such packing material may include, but is not limited to, spheres, beads, pellets, chips, fibers, sponges, pillows, and the like in any shape or form. In a particular embodiment, the packing is approximately spherical. Material for the packing may be metal, ceramic, plastic, glass and the like. In one embodiment, the packing material is glass or non-reactive metal. In a particular embodiment, the packing material is boro-silicate glass beads or stainless steel beads. The diameter of the beads may range from 20 to 2000 microns. In a particular embodiment, the beads may be in the range of 50 to 1000 microns.

Microparticle size is partially determined by the size and shape of individual packing material particles. Large and misfit packing materials generally pack together less closely than smaller packing material particles and produce larger gaps for the fluids to flow through. Larger gaps in the packing material produce larger microparticles and smaller gaps in the packing material produce smaller microparticles. The flow rate doesn't affect the size of the microparticles produced from a particular apparatus. Microparticles can vary in size, ranging from submicron to millimeter diameters. In one embodiment, microparticles are 1-200 microns in order to facilitate administration to a patient through a standard gauge needle. In a particular embodiment, the microparticles are between 10-100 microns.

The phases may be introduced into the packed bed emulsifier by any method. In one embodiment, the phases are introduced through pipes or tubes and may be pumped, forced by gas or another type of pressure source, fed by gravity or pulled by a vacuum at the discharge side of the packed bed emulsifier. The liquid phases may be carried by pipes comprising stainless steel, glass or plastic compatible with the solvents and temperatures used. The fluid phases may be at ambient temperature or at any temperature required between approximately freezing and approximately boiling for the particular fluid. The apparatus and methods of the present invention may be utilized at any pressure compatible with the equipment utilized. The pressure may be adjusted to whatever pressure is necessary to overcome the resistance of the packing bed and provide a flow rate in the laminar flow region.

Microparticles containing a biological or chemical agent are collected from the emulsion product of the packed bed apparatus via solvent extraction. Such techniques are known in the art.

The first and second phases of the present invention are any two fluids that are immiscible with one another. If a third phase is utilized in the production of microparticles, the resulting product from the first and second phases is combined with the third phase. In this case, the product from the combination of the first and second phases and the third phase are any two fluids that are immiscible with one another.

Solvents for the first phase may be any organic or aqueous solvents. Examples of solvents include, but are not limited to, water, methylene chloride, chloroform, ethyl acetate, benzyl alcohol, diethyl carbonate, methyl ethyl ketone and mixtures of the above. In a particular embodiment, the solvent is ethyl acetate or methylene chloride.

The first phase may comprise a solution of the biodegradable polymer and the biological or chemical agent as a solution or suspension. Alternatively the biological or chemical agent is dissolved or suspended in the second phase.

Solvents for the second phase may be any organic or aqueous fluid that is immiscible with the first phase. Examples include, but are not limited to, water, a water-based solution, an organic solvent, and the like. In a particular embodiment, the second phase contains water, an emulsion stabilizer and optionally a solvent. In another particular embodiment, the second phase contains water, one or more biological or chemical agents and optionally a water soluble polymer. In another particular embodiment, the second phase contains a second organic solvent, one or more biological or chemical agents and a polymer.

A holding tank or feed vessel may be utilized in the present invention to hold the first or second phases (See FIG. 2). The holding tanks or feed vessels may be jacketed or otherwise equipped to provide temperature control of the contents. A tube may run from each one through a pump and later merge with the tube from the other one to the entrance to the packed bed apparatus. The merge may also happen at the entrance of the packed bed apparatus or inside the packed bed apparatus itself. Additionally, the packed bed apparatus may include pumps or other means of moving the phases into and through the packed bed apparatus. The phases may flow from the holding tanks or feed vessels into the packed bed apparatus without pumps, by simple gravity, by pressure or by a vacuum from the other end of the packed bed apparatus, and the like. The tubes may further include addition of flow meters, feedback control, flow rate programming via programmed logic control, and the like.

Emulsion stabilizers of use in the present invention may include, but are not limited to, poly(vinyl alcohol), polysorbate, protein such as albumin, poly(vinyl pyrrolidone). In a particular embodiment, poly(vinyl alcohol) is used. The concentration of emulsifier may be in the range 0% to 20%, preferably 0.5% to 5%.

Biodegradable polymers of use in the present invention include, but are not limited to, poly(d,l-lactic acid), poly(l-lactic acid), poly(glycolic acid), copolymers of the foregoing including poly(d,l-lactide-co-glycolide) (PLGA), poly (caprolactone), poly(orthoesters), poly(acetals), poly(hydroxybutryate). In a particular embodiment, the biodegradable polymer is PLGA. PLGA may have a monomer ratio of lactide:glycolide in the range of about 40:60 to 100:0 or from about 45:55 to 100:0.

In a certain embodiment, the inherent viscosity of the biodegradable polymer may be in the range 0.1 to 2.0 dL/g. Preferably the range is from about 0.1 to about 1.0 dL/g. The biodegradable polymer is included at a concentration in the range 1% to 40% w/w, preferably in the range 5%-20% w/w.

Biological agents of use in the present invention may be any agent capable of having an effect when administered to an animal or human. In a particular embodiment, they include, but are not limited to, an organic molecule, an inorganic molecule, antiinfectives, cytotoxics, antihypertensives, antifungal agents, antipsychotics, antibodies, proteins, peptides, antidiabetic agents, immune stimulants, immune suppressants, antibiotics, antivirals, anticonvulsants, antihistamines, cardiovascular agents, anticoagulants, hormones, antimalarials, analgesics, anesthetics, nucleic acids, steroids, aptamers, hormones, steroids, blood clotting factors, hemopoietic factors, cytokines, interleukins, colony stimulating factors, growth factors and analogs, fragments thereof and the like.

Chemical agents of use in the present invention may be any synthetic or natural agent. In a particular embodiment, they include, but are not limited to, antioxidants, porosity enhancers, solvents, salts, cosmetics, food additives, textile-chemicals, agro-chemicals, plastisizers, stabilizers, pigments, opacifiers, adhesives, pesticides, fragrances, antifoulants, dyes, salts, oils, inks, cosmetics, catalysts, detergents, curing agents, flavors, foods, fuels, herbicides, metals, paints, photographic agents, biocides, pigments, plasticizers, propellants, solvents, stabilizers, polymer additives and the like.

The methods of the present invention are functional at any temperature within the operating range of the equipment, solvents and active agent. Factors that determine the appropriate temperature for a particular process include the optimum temperature for the two phases to be pumped through the packed bed apparatus. If a third phase is utilized, the temperature for the first packed bed apparatus may be the same or different than that of the second packed bed apparatus. The temperature needs to be such that the two phases are of a desirable viscosity. Additionally, the solubility of the polymer and active molecule may require an increase in temperature in order to produce a complete solution. The temperature may additionally be affected by the stability limit of the biological or chemical agent. Typical operating temperatures may range from 18 to 22 C, 15 to 30 C, 10 to 70 C, 0 to 96 C, and the like. In general, temperature may range from −273 to 150 C.

The microparticles of the present invention can be used for any purpose. In a particular embodiment, they are administered to a patient. They may be administered to patients in a single or multiple dose. The microparticles may also be administered in a single dose form that functions to further release the biological or chemical agent over a prolonged period of time, eliminating the need for multiple administrations.

The microparticles of the present invention can be stored as a dry material. In the instance of administration to a patient, prior to such use, the dry microparticles can be suspended in an acceptably pharmaceutical liquid vehicle, such as a 2.5 wt. % solution of carboxymethyl cellulose in water. Upon suspension, the microparticles may then be injected into the patient or otherwise utilized.

Definitions

For the purposes of the present invention, the following terms shall have the following meanings:

Moreover, for the purposes of the present invention, the term "a" or "an" entity refers to one or more of that entity; for example, "a protein" or "an estradiol metabolite molecule" refers to one or more of those compounds or at least one compound. As such, the terms "a" or "an", "one or more" and "at least one" can be used interchangeably herein. It is also to be noted that the terms "comprising," "including," and "having" can be used interchangeably. Furthermore, a compound "selected from the group consisting of" refers to one or more of the compounds in the list that follows, including mixtures (i.e. combinations) of two or more of the compounds.

For the purposes of the present invention, the term "biodegradable" refers to polymers that dissolve or degrade in vivo within a period of time that is acceptable in a particular therapeutic situation. This time is typically less than five years and usually less than one year after exposure to a physiological pH and temperature, such as a pH ranging from 6 to 9 and a temperature ranging from 25 C to 38 C.

For the purpose of the present invention, the term "packed bed apparatus" refers to any vessel containing packing material capable of creating an emulsion upon contact with two immiscible fluids.

For the purposes of the present invention, the term "active agent" refers to any biological or chemical agent.

Having generally described the invention, a further understanding can be obtained by reference to certain specific examples which are provided herein for purpose of illustration only and are not intended to be limiting unless otherwise specified.

EXAMPLES

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Preparation of Biodegradable Polymer Microspheres

A first phase containing 10% PLGA was prepared by dissolving 10 grams 85:15 PLGA (Medisorb 8515DLC01, Alkermes, Inc., 6960 Cornell Rd., Cincinnati, Ohio 45242) in 90 grams of ethyl acetate. The second phase was prepared by dissolving two grams of poly(vinyl-alcohol) (PVA) and 16 grams of ethyl acetate in 198 grams of water. Both solutions were placed inside separate temperature-controlled feed vessels at 20° C. (FIG. 2).

The second phase was pumped through a packed bed apparatus (6 mm Polytetrafluoroethylene (PTFE) tubing, 150 mm long, filled with 500μ glass beads) of the present invention at a rate of 1 ml/min. The first phase was pumped at the same time through the same packed bed apparatus at a flow rate of 1 ml/min. The emulsion was collected in an excess volume of water, the solvent was removed and the hardened microparticles separated.

The microspheres were analyzed by laser light scattering for size distribution with the following results:
Mean Diameter=46 μm (volume statistics)
D10=35 μm
D50=46 μm
D90=58 μm

Example 2: Preparation of 2-Methoxyestadiol (2ME) Microspheres

A first phase was prepared by dissolving 200 mg of 2ME and 400 mg of 50:50 PLGA in 7 ml of ethyl acetate. 2 grams of poly(vinyl-alcohol) (PVA) were dissolved in 198 grams of water to prepare the second phase. Both phases were then placed inside temperature-controlled water baths at 65° C.

The second phase was pumped through a packed bed apparatus (6 mm PTFE tubing, 150 mm long, filled with 500μ glass beads) of the present invention at a rate of 1.5 ml/min. The first phase was pumped at the same time through the same packed bed apparatus at a flow rate of 1 ml/min. The emulsion was collected inside a glass beaker where the solvent was removed from the emulsion droplets.

The hardened microspheres were centrifuged, and the microspheres were washed 3 times with water. The microspheres were analyzed for particle size distribution with the following results:
Mean Diameter=40 μm (volume statistics)
D10=27 μm
D50=40 μm
D90=53 μm

Example 3: Preparation of PEGylated Insulin Microspheres

A first phase was prepared by dissolving 213 mg of PEGylated insulin (U.S. Provisional Application No. 60/462,364 entitled "Method for Preparation of Site-Specific Protein Conjugates") and 748 mg of 45:55 PLGA in 10 ml of methylene chloride. Next, 2 grams of poly(vinyl-alcohol) (PVA) were dissolved in 198 grams of water to prepare the second phase.

The first phase was pumped through a packed bed apparatus (6 mm PTFE tubing, 150 mm long, filled with 500μ glass beads) of the present invention at a rate of 1.7 ml/min. The second phase was pumped at the same time through the same packed bed apparatus at a flow rate of 0.7 ml/min. The emulsion was collected inside a glass beaker where the solvent was removed by evaporation.

The finished microspheres were filtered and washed with water, and then dried open to the atmosphere overnight. The dried microspheres were analyzed for particle size distribution with the following results:
Mean Diameter=61 μm (volume statistics)
D10=42 μm
D50=60 μm
D90=79 μm

Example 4: Preparation of Double-Emulsion Microspheres

A first phase was prepared by dissolving 4.5 g of 65:35 PLGA in 40.5 g ethyl acetate. Next, a second phase was prepared by dissolving 225 mg ovalbumin in 7.5 g water. Next, 2 g of poly(vinyl-alcohol) (PVA) and 5 g of ethyl acetate were dissolved in 192 g of water to prepare the third phase.

The first phase was pumped through the same packed bed apparatus at a flow rate of 5.0 ml/min. The second phase was pumped through a packed bed apparatus (1 inch stainless steel tube, 200 mm long, filled with 50μ glass beads) of the present invention at the same time at a rate of 1.0 ml/min. The internal emulsion coming out of the first packed bed apparatus as a result of the mixture of the first and second phases was then directed into a second packed bed apparatus (½ inch stainless steel tube, 200 mm long, filled with 500μ glass beads) of this invention. The third phase was pumped at the same time through the second packed bed apparatus at a rate of 13 ml/min. The resultant emulsion product coming out of the second packed bed apparatus was collected inside a glass beaker where the solvent was removed.

The finished microspheres were filtered and washed with water, and then lyophilized overnight. The dried microspheres were analyzed for particle size distribution with the following results:
Mean=35 μm (volume statistics)
Median=35 μm (volume statistics)
Standard Deviation=13.5 μm

Example 5: Preparation and Scale-Up of a Packed Bed Apparatus

An apparatus for the production of microparticles containing Estradiol Benzoate with a particle size distribution in the range of 25-60 microns was made of stainless steel tubing, 1 inch in diameter, and 200 mm in length. The tubing was packed with glass beads with an average diameter of 375 microns.

A 15% PLGA phase one solution was prepared by dissolving 150 grams 85:15 PLGA (Medisorb 8515DLC01, Alkermes, Inc., 6960 Cornell Rd., Cincinnati, Ohio 45242) in 850 grams of ethyl acetate. 75 grams of estradiol benzoate was added to the solution and stirred at 60° C. until completely dissolved. Next, 20 grams of poly(vinyl-alcohol) (PVA) and 100 grams of ethyl acetate were dissolved in 1880 grams of water to form the second phase. Both solutions were placed inside separate temperature-controlled feed vessels at 60° C. (FIG. 2).

The second phase was pumped through the above packed bed apparatus at a rate of 30 ml/min. The first phase was pumped at the same time through the same packed bed apparatus at a flow rate of 30 ml/min. The emulsion was collected inside a tank where the solvent was removed.

The finished microspheres were filtered and washed with water, and then dried under vacuum. The dried microspheres were analyzed for particle size distribution with the following results:
Mean=38 μm (volume statistics)
Median=38 μm (volume statistics)
Standard Deviation=8.4 μm

Example 6: Scale Up of Batch Size for Making Estradiol Benzoate Microspheres In order to demonstrate the scalability of the Packed Bed apparatus and process, a 1 kg batch of microparticles containing Estradiol Benzoate were produced with a projected microparticle distribution range of 35-100 microns. A Packed Bed Apparatus was built of 1-inch stainless steel tubing, 200 mm in length and packed with glass beads having an average diameter of 500 microns.

A 16.7% PLGA first phase solution was prepared by dissolving 800 grams 85:15 PLGA (Medisorb 8515DLC01, Alkermes, Inc., 6960 Cornell Rd., Cincinnati, Ohio 45242)

in 3990 grams of ethyl acetate. 200 grams of estradiol benzoate was added and stirred at 60° C. until completely dissolved. Next, 100 grams of poly(vinyl-alcohol) (PVA) and 500 grams of ethyl acetate were dissolved in 9400 grams of water to form the second phase. Both solutions were placed inside separate temperature-controlled holding tanks at 60° C. (FIG. 2).

The second phase was pumped through the packed bed apparatus at a rate of 50 ml/min. The first phase was pumped at the same time through the same packed bed apparatus at a flow rate of 50 ml/min. The emulsion was collected inside a tank where the solvent was removed.

The finished microspheres were filtered and washed with water, and then dried under vacuum. The dried microspheres were analyzed for particle size distribution with the following results:

Mean=66 µm (volume statistics)
Median=66 µm (volume statistics)
Standard Deviation=21 µm Example 7: Scale Up of Packed Bed Apparatus and Flow Rates This example demonstrates the application of a Packed Bed Apparatus for making microspheres at higher flow rates. A new Packed Bed Apparatus was built with stainless steel tubing 2-inch in diameter, 200 mm in length, and packed with glass beads with an average diameter of 465 microns.

A 10% PLGA first phase solution was prepared by dissolving 130 grams 85:15 PLGA (Medisorb 8515DLC01, Alkermes, Inc., 6960 Cornell Rd., Cincinnati, Ohio 45242) in 1170 grams of ethyl acetate. Next, 30 grams of poly(vinyl-alcohol) (PVA) and 210 grams of ethyl acetate were dissolved in 2760 grams of water to form the second phase. Both solutions were placed inside separate temperature-controlled feed vessels at 50° C. (FIG. 2).

The second phase was pumped through the above packed bed apparatus at a rate of 300 ml/min. The first phase was pumped at the same time through the same packed bed apparatus at a flow rate of 300 ml/min. The emulsion was collected inside a tank where the solvent was removed.

The finished microspheres were analyzed for particle size distribution with the following results:

Mean=28 µm (volume statistics)
Median=30 µm (volume statistics)
Standard Deviation=9.8 µm.

All of the METHODS and APPARATUS disclosed and claimed herein can be made and executed without undue experimentation in light of the present disclosure. While the methods have been described in terms of particular embodiments, it will be apparent to those of skill in the art that variations can be applied to the METHODS and APPARATUS and in the steps or in the sequence of steps of the methods described herein without departing from the concept, spirit and scope of the invention. More specifically, it will be apparent that certain agents that are both chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

I claim:

1. A method of preparing microparticles, comprising: (a) preparing a first phase, said first phase comprising a solvent, active agent and a polymer; (b) preparing a second phase comprising a solvent; (c) passing said first phase and said second phase through a packed bed apparatus under laminar flow conditions, wherein the packed bed apparatus contains a packing material selected from the group consisting of metal, ceramic, plastic and glass, and wherein the packing material is spherical beads ranging in size from 20 to 1000 µm, and wherein said method results in the formation of microparticles; and (d) collecting said microparticles containing said active agent.

2. The method of claim 1, wherein said packing material is selected from the group consisting of glass and stainless steel.

3. The method of claim 1, wherein said first phase comprising a solvent is selected from the group consisting of an organic solvent and water.

4. The method of claim 3, wherein said organic solvent is selected from the group consisting of methylene chloride, chloroform, ethyl acetate, benzyl alcohol, diethyl carbonate and methyl ethyl ketone.

5. The method of claim 1, wherein said second phase comprising a solvent is selected from the group consisting of an organic solvent and water.

6. The method of claim 5, wherein said solvent is water.

7. The method of claim 1, wherein said second phase further comprises an emulsion stabilizer.

8. The method of claim 7, wherein said emulsion stabilizer is selected from the group consisting of poly(vinyl alcohol), polysorbate, protein and poly(vinyl pyrrolidone).

9. The method of claim 8, wherein said protein is albumin.

10. The method of claim 1, wherein said second phase further comprises a second solvent.

11. The method of claim 10, wherein said solvent is selected from the group consisting of an organic solvent and water.

12. The method of claim 1, wherein said active agent is selected from the group consisting of antioxidants, porosity enhancers, solvents, salts, cosmetics, food additives, textile-chemicals, agro-chemicals, plasticizers, stabilizers, pigments, opacifiers, adhesives, pesticides, fragrances, antifoulants, dyes, salts, oils, inks, cosmetics, catalysts, detergents, curing agents, flavors, foods, fuels, herbicides, metals, paints, photographic agents, biocides, pigments, plasticizers, propellants, solvents, stabilizers, polymer additives, an organic molecule, an inorganic molecule, antiinfectives, cytotoxics, antihypertensives, antifungal agents, antipsychotics, antibodies, proteins, peptides, antidiabetic agents, immune stimulants, immune suppressants, antibiotics, antivirals, anticonvulsants, antihistamines, cardiovascular agents, anticoagulants, hormones, antimalarials, analgesics, anesthetics, nucleic acids, steroids, aptamers, hormones, steroids, blood clotting factors, hemopoietic factors, cytokines, interleukins, colony stimulating factors, growth factors, growth factor analogs and fragments thereof.

13. The method of claim 1, wherein said polymer is selected from the group consisting of poly(d,l-lactic acid), poly(l-lactic acid), poly(glycolic acid), copolymers of the foregoing including poly(d,l-lactide-co-glycolide) (PLGA), poly(caprolactone), poly(orthoesters), poly(acetals) and poly(hydroxybutryate).

14. A method of preparing microparticles, comprising: (a) preparing a first phase, said first phase comprising a solvent and an active agent; (b) preparing a second phase comprising a solvent and a polymer; (c) preparing a third phase containing a solvent; (d) combining said first phase and said second phase to create an emulsion; (e) passing said emulsion through a packed bed apparatus under laminar flow conditions with said third phase, wherein the packed bed apparatus contains a packing material selected from the group consisting of metal, ceramic, plastic and glass, and wherein the packing material is spherical beads ranging in size from 20 to 1000 µm, and wherein said method results in the formation of microparticles; and (f) collecting said microparticles containing said active agent.

15. The method of claim 14, wherein said packing material is selected from the group consisting of glass and stainless steel.

16. The method of claim 14, wherein said first phase comprising a solvent is selected from the group consisting of an organic solvent and water.

17. The method of claim 16, wherein said first phase includes a water-based solution.

18. The method of claim 14, wherein said second phase comprising a solvent is selected from the group consisting of an organic solvent and water.

19. The method of claim 18, wherein said solvent is an organic solvent.

20. The method of claim 14, wherein said first phase further comprises an emulsion stabilizer.

21. The method of claim 20, wherein said emulsion stabilizer is selected from the group consisting of poly(vinyl alcohol), polysorbate, protein and poly(vinyl pyrrolidone).

22. The method of claim 21, wherein said protein is albumin.

23. The method of claim 14, wherein said second phase further comprises a second solvent.

24. The method of claim 23, wherein said solvent is selected from the group consisting of an organic solvent and water.

25. The method of claim 14, wherein said active agent is selected from the group consisting of antioxidants, porosity enhancers, solvents, salts, cosmetics, food additives, textile-chemicals, agro-chemicals, plasticizers, stabilizers, pigments, opacifiers, adhesives, pesticides, fragrances, antifoulants, dyes, salts, oils, inks, cosmetics, catalysts, detergents, curing agents, flavors, foods, fuels, herbicides, metals, paints, photographic agents, biocides, pigments, plasticizers, propellants, solvents, stabilizers, polymer additives, an organic molecule, an inorganic molecule, antiinfectives, cytotoxics, antihypertensives, antifungal agents, antipsychotics, antibodies, proteins, peptides, antidiabetic agents, immune stimulants, immune suppressants, antibiotics, antivirals, anticonvulsants, antihistamines, cardiovascular agents, anticoagulants, hormones, antimalarials, analgesics, anesthetics, nucleic acids, steroids, aptamers, hormones, steroids, blood clotting factors, hemopoietic factors, cytokines, interleukins, colony stimulating factors, growth factors, growth factor analogs and fragments thereof.

26. The method of claim 14, wherein said polymer is selected from the group consisting of poly(d,l-lactic acid), poly(l-lactic acid), poly(glycolic acid), copolymers of the foregoing including poly(d,l-lactide-co-glycolide) (PLGA), poly(caprolactone), poly(orthoesters), poly(acetals) and poly(hydroxybutryate).

27. The method of claim 14, wherein said first phase and said second phase create an emulsion in an apparatus selected from the group consisting of a packed bed apparatus, a mixer, a sonicator, a vortexer and a homogenizer.

28. The method of claim 1, wherein said packing material is glass.

29. A method of preparing microparticles, comprising: (a) preparing a first phase, said first phase comprising a solvent, active agent and a polymer; (b) preparing a second phase comprising a solvent; (c) passing said first phase and said second phase through a packed bed apparatus under laminar flow conditions, wherein the packed bed apparatus contains a packing material selected from the group consisting of metal, ceramic, plastic and glass, and wherein the packing material is spherical beads ranging in size from 20 to 1000 µm, and wherein said method results in the formation of microparticles; and (d) collecting said microparticles containing said active agent, wherein said microparticles are from about 1 µm to about 200 µm in diameter.

* * * * *